United States Patent [19]

Cucin

[11] Patent Number: 5,112,302
[45] Date of Patent: May 12, 1992

[54] METHOD AND APPARATUS FOR PERFORMING LIPOSUCTION

[76] Inventor: Robert L. Cucin, 8 E. 62nd St., New York, N.Y. 10021

[21] Appl. No.: 553,881
[22] Filed: Jul. 16, 1990
[51] Int. Cl.⁵ .............................................. A61B 17/00
[52] U.S. Cl. ....................................... 604/35; 604/902
[58] Field of Search ...................... 604/152, 35, 51, 72, 604/902; 128/752; 606/171

[56] References Cited

U.S. PATENT DOCUMENTS

| | | |
|---|---|---|
| 3,082,805 | 3/1963 | Royce . |
| 3,732,858 | 5/1973 | Banko . |
| 3,734,099 | 5/1973 | Bender et al. . |
| 3,955,579 | 5/1976 | Bridgman . |
| 3,994,297 | 11/1976 | Kopf . |
| 4,167,944 | 9/1979 | Banko . |
| 4,203,444 | 5/1980 | Bonnell et al. . |
| 4,311,140 | 1/1982 | Bridgman . |
| 4,314,560 | 2/1982 | Helfgott et al. . |
| 4,530,356 | 7/1985 | Helfgott et al. . |
| 4,536,180 | 8/1985 | Johnson . |
| 4,577,629 | 3/1986 | Martinez . |
| 4,589,414 | 5/1986 | Yoshida et al. . |
| 4,735,605 | 4/1988 | Swartz . |
| 4,775,365 | 10/1988 | Swartz . |
| 4,815,462 | 3/1989 | Clark . |
| 4,850,354 | 7/1989 | McGurk-Burleson et al. . |
| 4,886,491 | 12/1989 | Parisi et al. . |
| 4,919,129 | 4/1990 | Weber, Jr. ............................ 604/35 |
| 4,932,935 | 6/1990 | Swartz ................................ 604/902 |
| 4,938,743 | 7/1990 | Lee ..................................... 604/902 |

OTHER PUBLICATIONS

Body Contouring with Suction Lipectomy, by U. K. Kesselring, as published in Clinics in Plastic Surgery, vol. II, No. 3, Jul. 1984.
Illouz's Technique of Body Contouring by Lipolysis, by Yves-Gerard Illouz, as published in Clinics in Plastic Surgery, vol. II, No. 3, Jul. 1984.
The Rationalizatoin of Liposuction: Toward a Safer and More Accurate Technique, by R. de la Plaza et al., as published in Aesthetic Plastic Surgery, vol. 13, pp. 243-250, 1989.

*Primary Examiner*—Paul J. Hirsch
*Attorney, Agent, or Firm*—Hopgood, Calimafde, Kalil, Blaustein & Judlowe

[57] ABSTRACT

A method and apparatus is disclosed for mechanically-assisted liposuction treatment. The apparatus includes a hand-holdable housing, a cannula, and a reciprocation mechanism. The hand-holdable housing has a cavity adaptable for receipt of a portion of the cannula. The cannula has a distal end and a proximal end and at least one suction aperture about the distal end. The cannula also has a base portion which is operably associated with the proximal end and insertable within the cavity so that the cannula is free to reciprocate relative to the housing. The reciprocation mechanism is disposed within the housing and is operably associated with the cannula so that the cannula can be selectively caused to reciprocate relative to the housing. The cannula is releasably detachable from the hand-holdable housing to facilitate cleaning and sterilization of the cannula and the housing.

37 Claims, 5 Drawing Sheets

METHOD AND APPARATUS FOR PERFORMING LIPOSUCTION

BACKGROUND OF THE INVENTION

1. Field of Invention

The present invention relates generally to a method and apparatus for performing liposuction, and more particularly to a method and apparatus for performing liposuction in a mechanically assisted manner using powered expedients.

2. Brief Description of the Prior Art

Suction lipectomy, commonly known as liposuction or lipoxheresis, is a well known surgical procedure used for sculpturing or contouring the human body to increase the attractiveness of its form. In general, the procedure involves the use of a special type of curet known as a cannula, which is operably connected to a vacuum source. The cannula is inserted within a region of fatty tissue where removal thereof is desired, and the vacuum source suctions the fatty tissue through the suction aperture in the cannula and carries the aspirated fat away. Removal of fat cells by liposuction creates a desired contour that will retain its form.

Presently, there are two widely accepted techniques of liposuction and each may be practiced using a conventional liposuction cannula. The first and most common method proposed by Yves-Gérard Illouz and described in the paper "Illouz's Technique of Body Contouring by Lipolysis" in Vol. 3, No. 3, July 1984 of Clinics in Plastic Surgery, involves making regular tunnels at a depth of at least 1 centimeter under the skin. According to this method, one or two insertions are made, with radial excursions of the cannula into the fatty tissue of the patient. The result is a multitude of concomitant sinuses formed below the subcutaneous fatty tissue, leaving intact as far as possible the connections between the skin and underlying tissue, thereby retaining the blood vessels, the lymphatics and the nerve endings. The second method is the original liposuction procedure proposed by U. K. Kesselring, described in "Body Contouring with Suction Lipectomy", in Vol. 11, No. 3, July 1984, Clinics in Plastic Surgery. According to the technique, an entire layer of regular, deep fat is removed by aspiration through the cannula, leaving a smooth, deep surface of the residual panniculus. The space thus created is then compressed, optimally followed by skin retraction.

Both of these prior art liposuction techniques require that the surgeon push and pull the entire cannula back and forth almost twenty times for each insertion made. Typically, twenty to thirty tunnels are made. This is necessary to ensure even removal of fat in the targeted region. During this procedure, the surgeon typically massages the flesh in the area of the aperture in the cannula, while at the same time, thrusting the rod in and out of the tunnel. Due to the trauma involved during the procedure, the patients' skin turns black and blue for several weeks. Due to the physically exacting nature of the procedure, the surgeon typically comes out of an operating room extremely tired and suffers from muscular fatigue which prevents him from performing for some time thereafter, the delicate operations involved in ordinary plastic surgery.

In an attempt to solve the above-described problem, U.S. Pat. Nos. 4,735,605, 4,775,365 and 4,792,327 to Swartz disclose an assisted lipectomy cannula having an aspiration aperture which effectively travels along a portion of the length of the cannula, thereby obviating the necessity of the surgeon to repeatedly push the cannula in and out of the patients' subcutaneous tissue where fatty tissue is to be removed. While this assisted lipectomy cannula can operate on either air or electric power, it nevertheless suffers from several significant shortcomings and drawbacks. In particular, the device requires an outer tube with an elongated slot and a inner tube having a spiral slot which must be rotated inside the outer tube to effectuate a traveling aspiration aperture. In addition to this construction posing great difficulties in cleaning and sterilization and undue complexity of the cannula lumen itself, exact relocation of the traveling aperture appears to render this cannula highly ineffective in fat aspiration.

Accordingly, there is a great need in the art for a mechanically assisted lipectomy cannula which overcomes the shortcomings and drawbacks of prior art lipectomy apparatus.

Thus, it is a primary object of the present invention to provide an improved method and apparatus for performing liposuction which assists the surgeon in the removal of fat and other subcutaneous tissue (such as but not restricted to gynecomastia) from surrounding tissue, with increased control and without promoting physical fatigue.

It is another object of the present invention to provide such apparatus in the form of a hand-holdable liposuction instrument in which the cannula and its accompanying aspiration aperture or apparatus reciprocates back and forth relative to a hand-holdable housing.

It is a further object to provide such a liposuction instrument in which the rate of reciprocation and the amount of excursion of the cannula are selectively adjustable by the surgeon during the course of operation.

An even further object of the present invention is to provide such a liposuction instrument which can be driven by air or electricity.

A further object of the present invention is to provide such a liposuction instrument, in which the cannula can be simply detached from the hand-holdable housing for ease of replacement and/or sterilization.

An even further object of the present invention is to provide an improved method of performing liposuction, in which the cannula is automatically reciprocated back and forth relative to the hand-holdable housing, to permit increased control over the area of subcutaneous tissue where fatty and other soft tissue is to be aspirated.

These and other objects of the present invention will become apparent hereinafter.

SUMMARY OF INVENTION

According to one aspect of the present invention, there is provided apparatus including a hand-holdable housing, a cannula, and a reciprocation means. The hand-holdable housing has a cavity adaptable for receipt of a portion of the cannula. The cannula has a distal end and a proximal end and at least one suction aperture about the distal end. The cannula also has a base portion which is operably associated with the proximal end and insertable within the cavity so that the cannula is free to reciprocate relative to the housing. The reciprocation means is disposed within the housing and is operably associated with the cannula so that the cannula can be selectively caused to reciprocate relative to the housing. The cannula is releasably detachable from the hand-holdable housing to facilitate cleaning and sterilization of the liposuction device.

In one embodiment, the reciprocation means is realized using gas driven piston-type motor, which causes the cannula to reciprocate relative to the hand-holdable housing and means are provided for controlling the amount of cannula excursion, as well as rate of cannula reciprocation.

In another embodiment, a pair of gas-driven piston-type motors are used to realize the reciprocation means. A mechanically-operated gas flow control device is provided for automatically controlling the flow of gas to effectuate cannula reciprocation.

In yet another embodiment, the hand-holdable housing is realized in the form of a pistol, having a barrel portion and a handle portion, facilitating the use of a rotary type motor without compromising desired amounts of cannula excursion.

As a result of the present invention aspiration of fat and other soft tissue can be achieved without causing fatigue of the surgeon. Also, simplified mechanical construction provides improved performance and simplified cleaning, sterilization, and maintenance.

DETAILED DESCRIPTION OF THE DRAWINGS

For a fuller understanding of the objects of the present invention, reference is made to the detailed description of the illustrative embodiments which are to be taken in connection with the accompanying drawings, wherein.

DETAILED DESCRIPTION OF THE PREFERRED EMBODIMENTS

With reference to FIGS. 1–3 and 7, the first embodiment of the liposuction device of the present invention will be described. In general, the liposuction device 1 comprises a hand-holdable housing 2, a detachable cannula 3, and a reciprocation means 4 for causing the cannula 3 to reciprocate relative to the housing 2.

Figures 6, 6B, 6C, 6D, 7, 8A, 8B:
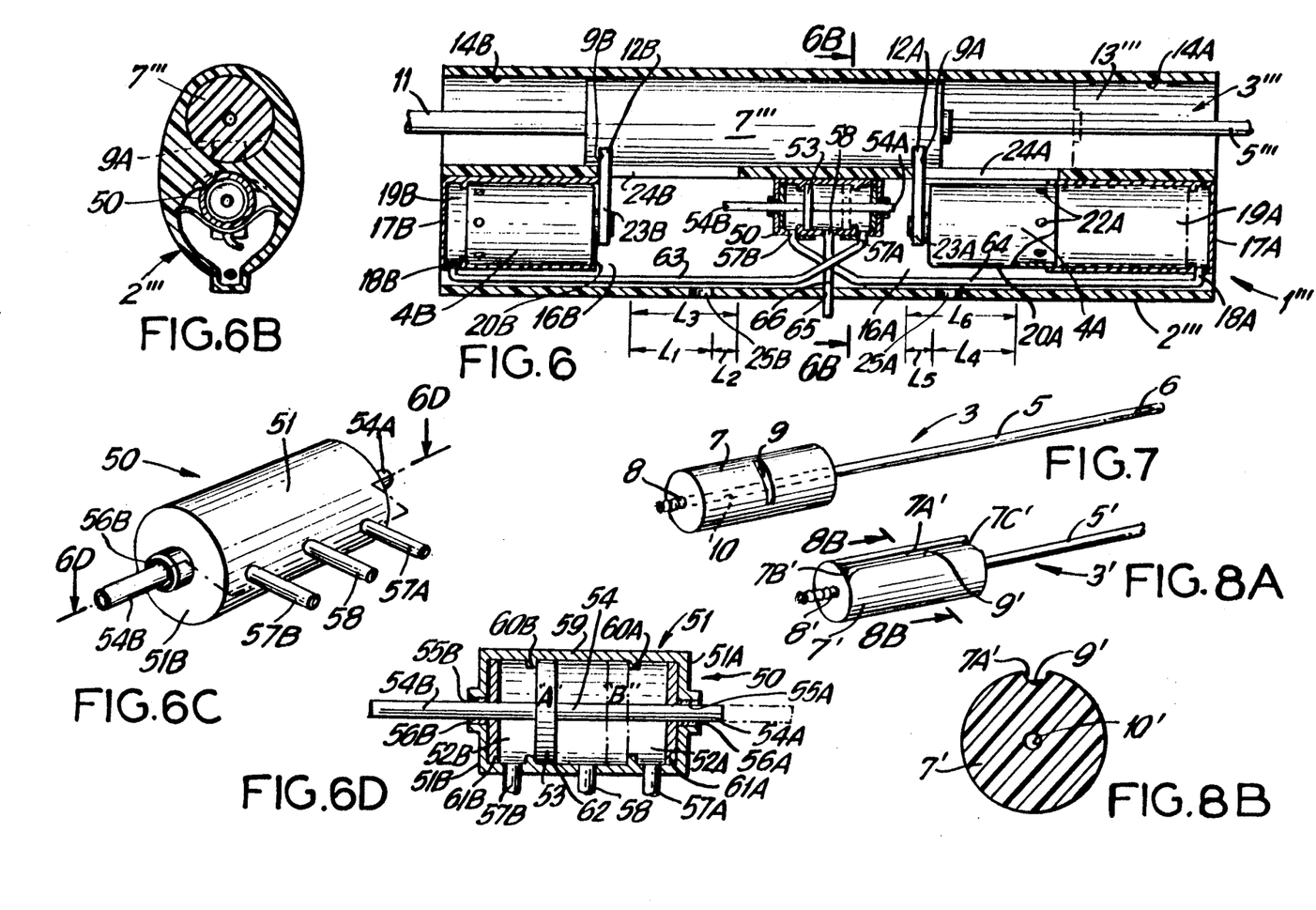
FIG. 6 is cross-sectional view of a fourth embodiment of the liposuction device of the present invention, illustrating the use of a pair of gas driven piston-type motors and a mechanically-operated gas flow control device disposed in its first state of operation.
FIG. 6B is a cross-sectional view of the liposuction device of the present invention, taken along line 6B—6B of FIG. 6.
FIG. 6C is a perspective view of the preferred embodiment of the mechanically-operated gas flow control device illustrated in FIG. 6.
FIG. 6D is a cross-sectional view of the gas flow control device of the present invention, taken along line 6D—6D of FIG. 6C.
FIG. 7 is a perspective view of a cannula intended for use in connection with the first, third, fourth and fifth embodiments of the liposuction device of the present invention.
FIG. 8A is a perspective view of a cannula intended for use with the second embodiment of the liposuction device of the present invention.
FIG. 8B is a cross-sectional view of the cannula of the present invention, taken along lines 8B—8B of FIG. 8A.

As illustrated in greater detail in FIG. 7, cannula 3 of the present invention comprises an elongated tube 5 having an aspiration (i.e., suction) aperture 6 at its distal end and a base 7 operably associated with the proximal end of tube 5. Preferably, cannula base 7 has an outlet port 8 formed at its remote end, and a notch or slot 9 formed in its central most portion, as shown. As will be described in greater detail hereinafter, notch 9 functions to releasably receive a portion 12 of actuation element 23, in order to actuate reciprocation of cannula 3 within housing 2. The shape of cannula base 7 is preferably cylindrical and will match the bearing surfaces which guide the cannula as it is caused to reciprocate within housing 2. As illustrated, cannula 3 has a continuous passageway 10 which extends from aspiration aperture 6 to outlet port 8 for transporting aspirated fat tissue through aperture 6 to a conventional vacuum source (not shown). To achieve this function, the vacuum source is connected to outlet port 8 using preferably optically transparent, semi-flexible tubing 11.

Figures 1, 2, 3:
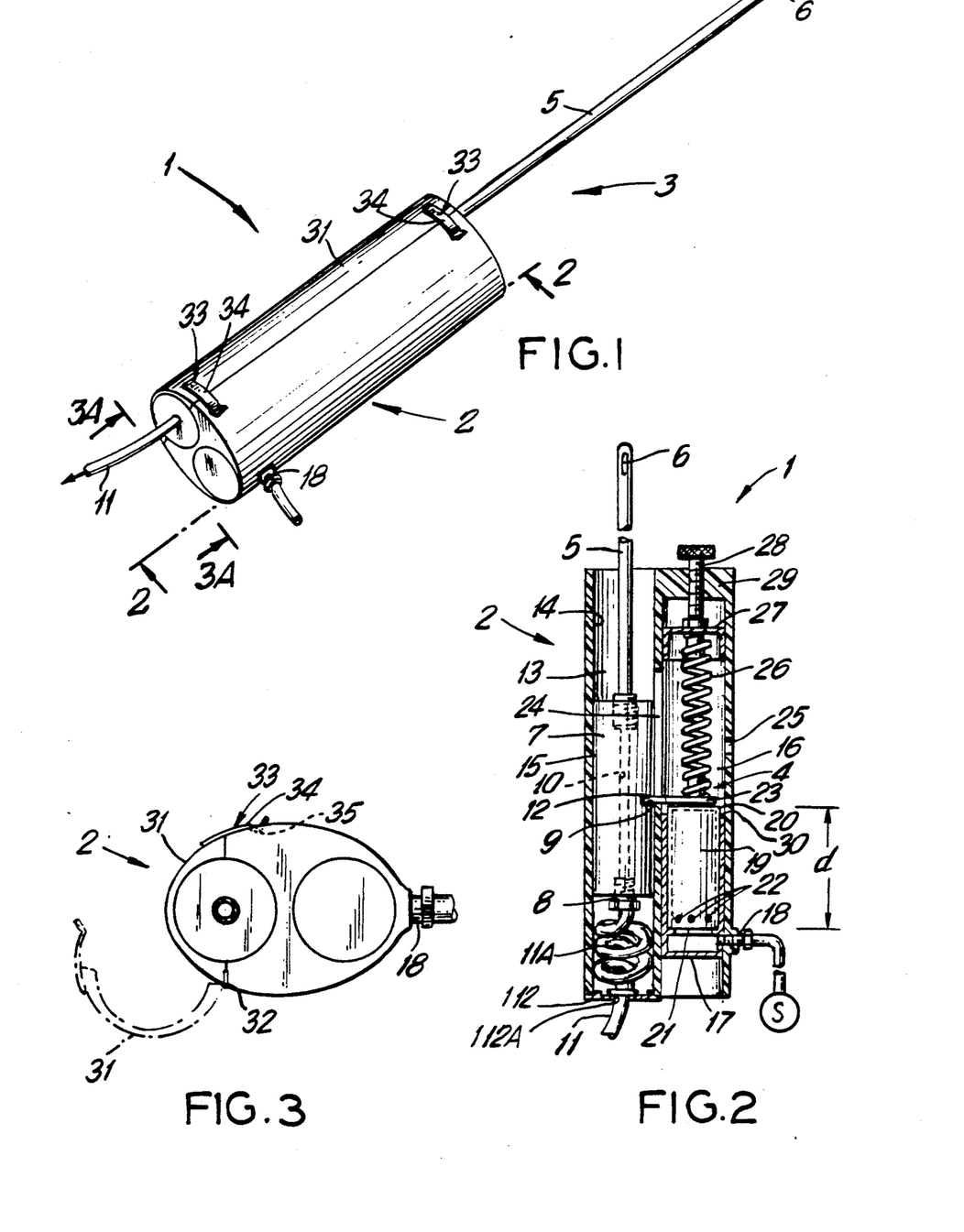
FIG. 1 is a perspective view of one embodiment of the liposuction device of the present invention.
FIG. 2 is a cross-sectional view of the liposuction device of the present invention taken along line 2—2 of FIG. 1.
FIG. 3 is a cross-sectional view of the liposuction device of the present invention, taken along line 3A—3A of FIG. 1, showing the cannula retained within the cannula cavity of the hand-holdable housing, and alternatively showing the hingedly connected cover panel of the hand-holdable housing disposed in an open position for removal of the cannula therefrom.

As shown, the gross geometry of the housing 2 is preferably that of an ellipsoid, however, other geometries such, for example, as a cylindrical structure, can be used in practicing the present invention. Housing 2 has a cannula cavity generally indicated by reference numeral 13, and has generally cylindrical bearing surfaces 14 which match the outer bearing surface 15 of cannula base 7, to permit sliding movement of cannula 3 within cavity 13. While cylindrical bearing surfaces have been selected in the preferred embodiment, use of other forms of bearing surfaces (e.g., rectangular or triangular) are contemplated. To minimize friction, bearing surfaces 14 and 15 may be coated with a Teflon ® or functionally equivalent coating, to facilitate easy sliding of cannula base 7 within cavity 13 with low wear.

Cannula 3 and other embodiments of the cannula of the present invention can be made of a variety of materials, including, for example, stainless steel and plastic. Stainless steel offers the advantage of being easily cleaned and sterilizable, while plastic offers the advantage of low manufacturing cost and disposability. Preferably, when making the cannula from a suitable plastic material, injection molding processes can be used to form an integrally molded cannula having desired characteristics. The molded cannula would be subsequently sterilized and packaged. In the surgical environment, the surgeon can simply remove a selected cannula from its sterilized package, and insert the cannula into the cannula cavity of a liposuction device of the present invention.

As illustrated in FIG. 3, housing 2 is provided with a hinged cover 31. Hinged cover 31 allows cannula cavity 13 to be opened and accessed and cannula 3 to be selectively installed in and removed from housing cavity 13. Cover panel 31 has a semi-circular cross-sectional geometry and is connected to the remainder portion of the housing 2 by a conventional hinge means 32. To secure cover panel 31 to the remainder of housing 2, a releasable locking means 33 is provided at the interface of hinge cover 31 and the remainder portion of housing 2, as shown. Releasable locking means 33 can be realized in a variety of ways, including, for example, using a spring biased clamp element 34 which engages in a notch 35 formed in the external surface of the remainder portion of the housing 2, as illustrated in FIG. 3.

To effectuate reciprocation of cannula 3 within cannula cavity 13, a gas or electrically driven motor(s), in general, can be used to realize the reciprocation means 4 of present invention. In the embodiments illustrated in FIGS. 1-6, one or more gas driven piston-type motors are employed. In the embodiment illustrated in FIGS. 9 through 9E, a rotary-type motor is used to realize reciprocation means 4 of the present invention.

As illustrated in FIG. 2, a piston-type motor 4 is mounted within a motor cavity 16 provided adjacent cannula cavity 13 of housing 2. In general, motor 4 comprises a chamber housing 17 having a gas inlet port 18 and an inner chamber generally indicated by reference numeral 19. Slidably received within the inner chamber of housing 17 is a movable piston 20 having formed in its lower most wall 21, one or more gas outlet ports 22. Mounted to the top portion of movable piston 20, is actuation element 23 which projects through a longitudinally disposed slot 24 formed in the bearing wall 14 of cannula cavity 13. Projection 12 of actuation element 23 through the slot 24, is received within notch 9 formed in cannula base 7 and operably associates cannula 3 with motor 4.

As illustrated in FIG. 2, chamber housing 17 is fixedly disposed within motor cavity 16. Motor cavity 16 is also provided with at least one port 25 for ventilating to the ambient environment, gas released from movable piston 20 upon reaching it maximum displacement or excursion. Movable piston 20 is biased in the direction of chamber housing 17 by way of a spring biasing element 26. The compliance of spring biasing element 26 can be adjusted by moving the position of slidable wall 27 by rotating, for example, threaded element 28 passing through a portion 29 of the housing 2, as shown. With this arrangement, adjustment of wall 27, closer to or farther from chamber housing 17, results in decreasing or increasing, respectively, the compliance of spring biasing means 26. This, in turn, provides a simple, yet reliable way in which to control the rate of reciprocation of movable piston 20, and thus the rate of reciprocation of cannula 3 relative to housing 2.

In order that cannula 3 may reciprocate within cannula cavity 13 without occasioning reciprocating movement of vacuum tubing 11, surplus tubing portion 11A is provided between tubing 11 and outlet port 8, as shown. An end cap 112 is installed into the end of cylindrical cavity 13 and has an aperture 112A which permits tubing 11 to pass therethrough. A relief is provided to tubing 11 on the inside portion of cap 112, to restrain movement of tubing 11 relative to end cap 12. As cannula 3 is displaced away from end cap 112, surplus portion 11A expands longitudinally and as cannula is displaced towards cap 112, surplus portion 11A contracts into a configuration shown in FIG. 2.

The manner of operation of piston-type motor 4 is described as follows. Gas, such as pressurized air or $N_2$ gas, is introduced under constant pressure to inlet port 18 of chamber housing 17. As the gas fills up the volume enclosed by the interior walls of the movable piston and the chamber, inner chamber 19 begins to expand, forcing movable piston 20 upwardly against the biasing force of spring biasing element 26. When movable piston 20 is displaced sufficiently enough from chamber housing 17 so that gas within expanding chamber 19 can be released through gas exit port 25 to the ambient atmosphere, piston 20 will be forced back downwardly into chamber housing 17 at a rate inversely proportional to the compliance of spring biasing element 26. Subsequently, chamber 19 will again fill up with gas, piston 20 will again be displaced and gas subsequently vented, whereupon reciprocating displacement of piston 20 will be repeated again in a cyclical manner. Since movable piston 20 is operably connected with cannula base 7 by way of actuation element 23, this reciprocating movement of piston 20 results in reciprocating movement of cannula 3 within cannula cavity 13.

As illustrated in FIG. 2, the amount of excursion that the piston is permitted to undergo before gas venting and subsequent downward piston movement occurs, is determined by the distance "d" defined between gas output port 22 and top wall surface 30 of chamber housing 17. Typically, a cannula excursion distance of three inches, for example, will necessitate that the parameter d, defined above, also be about three inches.

Figure 4:
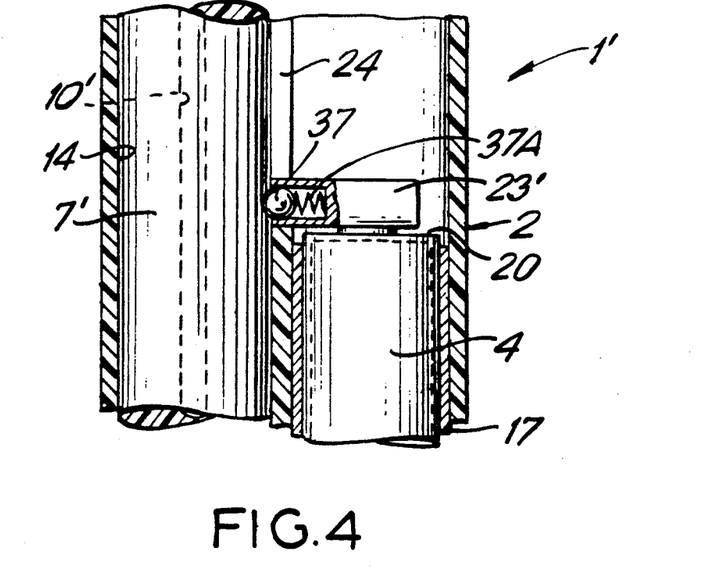
FIG. 4 is a cross-sectional view of a portion of a second embodiment of the liposuction device of the present invention, illustrating an alternative cannula retention means.

In FIG. 4, a second embodiment of the liposuction device of the present invention is shown. Liposuction device 1' has an alternative cannula retention means while inhering all of the structure features of the first embodiment illustrated in FIGS. 1-3. In particular, liposuction device 1' does not have a hingedly connected cover panel, but rather has a permanently enclosed cannula cavity 13. Instead of having an actuation element that projects beyond the cannula cavity wall 14, actuation element 23' projects essentially flush with the elongated slot 24, and has a spring biased ball bearing 37 which projects slightly beyond the cannula cavity wall surface 14, as shown in FIG. 4.

In FIG. 8A, there is shown a cannula 3' for use with a permanently enclosed cannula cavity. Notably, elements of cannula 3' which correspond to cannula 3, are indicated by primed reference numbers. In this embodiment, instead of having a deep slot, cannula base 7' has a deeply formed spherical indent 9' which receives ball bearing 37 biased by spring 37A in the projection of actuation element 23'. To facilitate guiding ball bearing 37 into indent 9', a longitudinally extending groove 7A' in base 7 is formed. Also, as shown, widened recess portions 7B' and 7C' are formed at opposite ends of groove 7A' to facilitate insertion of ball bearing 37 in groove 7A'. When cannula 3' is slid into the matched cannula cavity 13', ball bearing 37 snaps into indent 9' to establish a locked position. Notably, biased ball-bearing 37 and matched spherical indentation 9' serve to retain cannula 3' within cannula cavity 13', and in cooperation with actuation element 23 and indent 9', effectuates reciprocation of cannula 3' when piston 20 is caused to reciprocate. Cannula 3' is simply removed from cannula cavity 13' by quickly pulling on cannula tube 5' with a modest degree of force, to overcome the bias force of engaged ball bearing 37. This retention mechanism can also provide a safety release feature, in that if cannula 5 becomes snagged during an operation, it will disengage from the reciprocation means 4 if a proper spring biasing force is selected for ball bearing 37.

Figure 5:
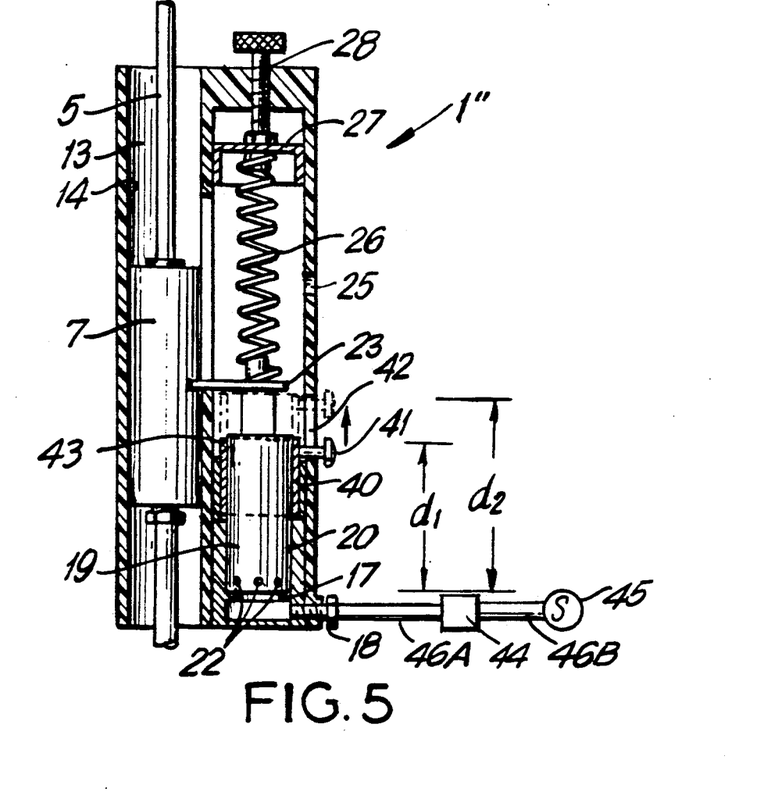
FIG. 5 is a cross-sectional view of a third embodiment of the liposuction device of the present invention, illustrating the cannula excursion control feature of the preferred embodiment.

In order to selectively adjust the amount of cannula excursion permitted during a liposuction operation, piston-type motor 4 can be modified, as shown in FIG. 5, to produce a third embodiment of the liposuction device of the present invention. As illustrated in FIG. 5, the basic structure of liposuction device 1" is similar to that shown in FIGS. 1 through 3, except that a user-adjustable intermediate housing wall 40 is disposed between the inner walls of chamber housing 17 and the outer walls of movable piston 20. Intermediate housing wall 40 is operably associated with an excursion selection means realized as a slidable member 41 fixedly attached to the upper portion of intermediate housing wall 40. Preferably, slidable member 41 extends through a slot 42 formed in the wall of housing 2 and can be slid, for example, by movement of the surgeon's thumb. The function of intermediate housing wall 40 is to effectively raise the height of the chamber housing wall, and thus selectively increase distance d, defined as the distance between gas outlet port 22 in piston 20 and upper portion 43 of the chamber housing wall. In this way, movable piston 20 must undergo a larger displacement before compressed gas will be released and piston 20 permitted to be forced downwardly under the biasing force of biasing spring element 26.

As illustrated in the embodiment shown in FIG. 5, it is also possible to control the rate of reciprocation by controlling the rate of gas flow entering chamber 19 of piston-type motor 4. This can be achieved using a conventional gas flow regulation device 44 inserted between source of gas 45 and inlet port 18 of chamber housing 17. As shown, tubing sections 46A and 46B are used to achieve fluid communication between these elements. Typically, cannula reciprocation rates will be in the range of 30 to 90 reciprocation cycles per minute, and the corresponding gas flow rates will depend on parameters including, for example, the compliance of biasing spring 26, the volume of movable piston and chamber housing, the cross-sectional diameter of gas inlet port 18, and the cross-sectional diameter of gas outlet ports 22 in the piston.

Referring to FIGS. 6 through 6D, there is shown a fourth embodiment of the liposuction device of the present invention. In liposuction device 1''', housing 2 and cannula 3 are generally similar to those of the previously described embodiments, with the exception of several differences which will be described below.

As illustrated in FIG. 6, a pair of piston-type motors 4A and 4B of the type generally indicated in FIGS. 1 through 5 are fixedly installed within respective motor cavities 16A and 16B of housing 2. Each piston-type motor 4A and 4B has a respective chamber housing and movable piston, indicated by 17A and 17B, and 20B and 20B, respectively. Actuation elements 23A and 23B are fixedly connected to respective pistons 20A and 20B and project through respective elongated slots 24A and 24B formed in respective cannula cavity walls 14A and 14B, in a manner similar to that described in connection with the embodiments shown in FIGS. 1, 2, 3 and 5. While not shown in FIG. 6, preferrably a rod or bar is fixedly attached between actuation elements 23A and 23B in order to maintain them a fixed distance apart, so as to facilitate operable connection of the cannula with the actuation elements in the manner as described below. Notably, this embodiment will also include a hinged cover panel (not illustrated), in a manner similar to that described in the first and second embodiments.

As illustrated in FIG. 6, cannula base 7''' has first and second receiving slots or notches 9A and 9B, into which projections 12A and 12B of respective actuation elements 23A and 23B are received. Such operable connections between movable pistons 20A and 20B and cannula base 7''' enables cannula 3''' to reciprocate relative to housing 2 when actuation elements 23A and 23B are caused to reciprocate relative to respective gas driven motors 4A and 4B.

In order to fill and vent chambers 19A and 19B of the first and second piston motors to effect cyclical reciprocating motion of actuation elements 23A and 23B and thus cannula 3''', a mechanically-operated gas flow control device 50 is employed in operable association with gas inlet ports 18A and 18B, a source of pressurized gas (not shown), and movable pistons 20A and 20B.

As illustrated in greater detail in FIGS. 6C and 6D, gas flow control device 50 comprises a shuttle valve housing or casing 51, having first and second shuttle chambers 52A and 52B. These shuttle chambers are separated by a shuttle valve member 53 which is attached to a slidable shaft 54. As illustrated in FIG. 6 and 6D, shuttle valve member 53 is slidable between two positions or states "A" and "B". Shaft 54 extends through bores 55A and 55B formed in shuttle chamber end walls 51A and 51B respectively, in which seals 56A and 56B are installed in a conventional manner. When the shuttle valve 53 is centrally disposed in casing 51 between states shaft ends 54A and 54B protrude equally beyond respective bores 55A and 55B. Adjacent one end of side wall 59, a first gas exit port 57A is formed, whereas adjacent the other end of wall 59, a second gas exit port 57B is formed, as shown. At about intermediate the end walls, a gas inlet port 58 is formed in the shuttle chamber side wall 59. A pair of annulus-shaped shuttle valve stops 60A and 60B are formed at opposite end portions of the inside of cylindrical wall 59. These stops 60A and 60B serve to stop sliding movement of shuttle valve 53 when shaft 54 is displaced in one of two possible axial directions by actuation elements 23A and 23B, respectively, as shown in FIG. 6. As will be discussed hereinafter in greater detail, it is these actuation elements 23A and 23B which displace shaft 54 and thus shuttle valve 53 between one of two states as movable pistons 20A and 20B are caused to reciprocate. Preferably, at least a portion of shuttle valve 53 is formed of a ferromagnetic material so that ferrous end walls 61A and 61B will attract ferromagnetic shuttle valve 53 and pull it against one of stops 60A and 60B and into gas flow state A or B, i.e., when shuttle valve 53 is brought into proximity therewith upon displacement of shaft 54 by one of actuation elements 23A and 23B. Peripheral side surfaces of shuttle valve 53 are provided with seals 62 to ensure a gas seal between shuttle chambers 52A and 52B.

As illustrated in FIG. 6, first gas exit port 57A of device 50 is in a fluid communication with second chamber housing 17B by gas channel 63, whereas second gas exit port 57B is in fluid communication with first chamber housing 17A by gas channel 64. In the illustrated embodiments, gas inlet port 65 is formed through housing 2''' and is in fluid communication with gas inlet port 58 by gas channel 66. Notably, chamber housings 17A and 17B, shuttle valve housing 51, gas channels 63, 64 and 66 can be realized as discrete elements, as shown or as integrally formed elements which are part of the interior of hand-holdable housing 2''' itself.

The principal function of gas flow control device 50 is to control the flow of gas to pistons 20A and 20B so that only one of the gas pistons is actively driven at a time. The manner of operation of gas flow control device 50 in cooperation with the displacement of pistons 20A and 20B, will now be described.

Owning to the fact that shuttle valve 53 is magnetically biased to be in essentially one of two possible positions, or gas flow states, gas will initially be caused to flow into one of piston-chamber housings 52A or 52B, and cause its respective piston and actuation element to move away from its respective chamber housing. Only along a small portion of the piston excursion will shuttle valve shaft 54 and thus shuttle valve 53, be displaced within shuttle valve housing 51 as the actively driven piston is displaced upon buildup of pressurized gas within its respective chamber. To illustrate this cyclical process, it will be assumed that gas flow control valve 50 is initially in state A, as shown in FIG. 6. Here, piston 20A has reached its maximal displacement and pressurized gas within the chamber 19A is substantially vented through gas outlet port 22A in piston wall, and through ports 25A and 25B in housing 2'''. In this position (state A), shuttle valve 53 is magnetically biased against stops 60B so that gas is caused to flow from gas source (not shown), through first shuttle chamber 52A, into second chamber housing 17B. With shuttle valve 53 in this state, gas pressure is allowed to build up in chamber 19B, displacing piston 20B and actuation element 23B away from second chamber housing 17B, as indicated by the reference arrow. Therewhile, cannula base 7''' and piston 20A are caused to undergo an excursion within cannula cavity 13''', commensurate with the active travel) defined over length $L_1$, shuttle valve 53 remains in state A against stop 60B.

Then over piston excursion $L_2$, actuation extension 70B contacts shaft end 54B and displaces shuttle valve 53 away from stop 60B to about mid-position in shuttle housing 51, approximately over input port 58, at which point magnetic shuttle valve 53 is pulled toward ferrous plate 61A into state B and against stop 60A, as shown in FIG. 6. At this phase in the cycle, piston 20A is fully protracted from chamber housing 17A, while piston 20B is fully protracted from chamber housing 17B and displaced a distance $L_3$ from the upper portion thereof (i.e., $L_3 = L_1 + L_2$). In State B, gas flow control device 50 directs the flow of pressurized gas from a source (not shown), along channel 66, through second shuttle chamber 52B and into piston chamber housing 17A.

Magnetically biased shuttle valve 53 remains in state B as chamber housing 17A fills with pressurized gas, expanding the chamber 19A and displacing piston 20A away from chamber housing 17A while causing piston 20B to retract back into its chamber housing 17B. All the while, cannula base 7''', being operable associated with actuation elements 23A and 23B, undergoes a commensurate amount of excursion within cannula cavity 13'''. When piston 20A is displaced an amount of distance $L_4$, actuation element 23A contacts shaft end 54A and displaces the shuttle valve 53 a small distance $L_5$, at which point magnetic shuttle valve 53 is pulled towards ferrous plate 61B, into state A and against stop 60A, as shown in phantom lines in FIG. 6. At this phase in the cycle, piston 20B is fully retracted within chamber housing 17B while piston 20A is fully protracted from chamber housing 17A and displaced at a distance $L_6$ from the upper portion thereof (i.e., $L_6 = L_4 + L_5$). In state A, gas flow control device 50 directs the flow of pressurized gas from a source (not shown), along channel 66, through first shuttle chamber 52A and into piston chamber housing 19B. Magnetically biased shuttle valve 53 remains in state A as chamber housing 17B fills with pressurized gas, expanding chamber 19B displacing piston 20B away from the chamber housing 17B, while causing piston 20A to retract back into its piston chamber housing 17A. All the while, cannula base 7''', being operatably associated with actuation elements 23A and 23B, undergoes a commensurate amount of excursion within the cannula cavity 13. With a preselected gas pressure and flow rate set at gas inlet port 65 of housing 2''', the above-described process of gas filling, venting and flow control, occurs automatically at a corresponding rate resulting in periodic reciprocation of cannula 3''' relative to hand-holdable housing 2'''.

Figures 9, 9D:
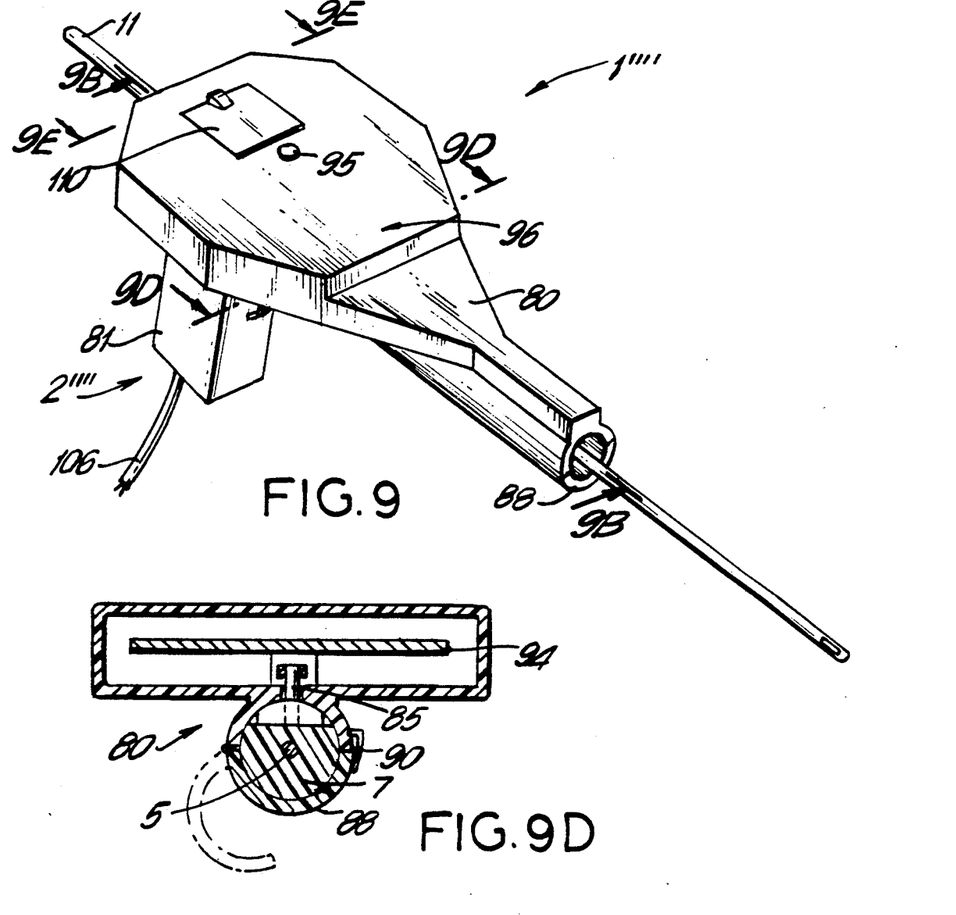
FIG. 9 is a plan view of a fifth embodiment of the liposuction device of the present invention, having a hand-holdable housing realized in the form of a pistol-shaped structure having detachable barrel and handle portions.
FIG. 9D is a cross-sectional view of the liposuction device of the present invention, taken along lines 9D—9D of FIGS. 9A and 9B showing the rotary drive wheel of the cam mechanism in operable association with the actuation element which projects through the cannula cavity and is engaged in the slotted base portion of the cannula, and also showing in phantom lines the cover panel of the barrel portion disposed in an open configuration permitting insertion or removal of a cannula of the present invention.
Figures 9A, 9B, 9C:
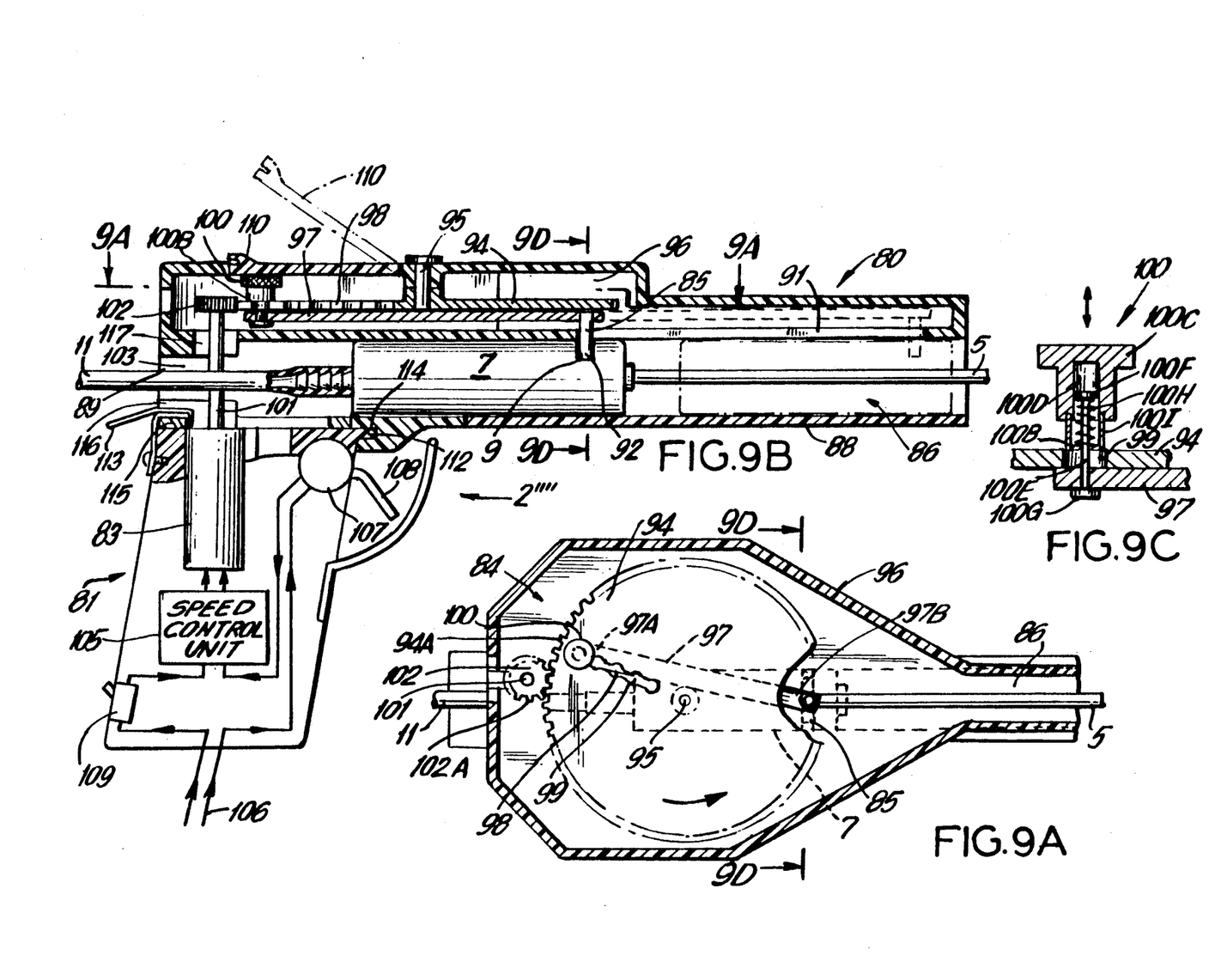
FIG. 9A is a partial cross-sectional view of the liposuction device of the present invention taken along line 9A—9A of FIG. 9B, showing the cam mechanism of the present invention.
FIG. 9B is an elevated cross-sectional view of the liposuction device of the present invention, taken along line 9B—9B of FIG. 9, showing the cannula disposed at a first position within the cannula cavity of the hand-holdable housing, and the rotary motor and speed control unit in the handle portion.
FIG. 9C is a cross-sectional view of a portion of the cannula excursion control means of the present invention.
Figure 9E:
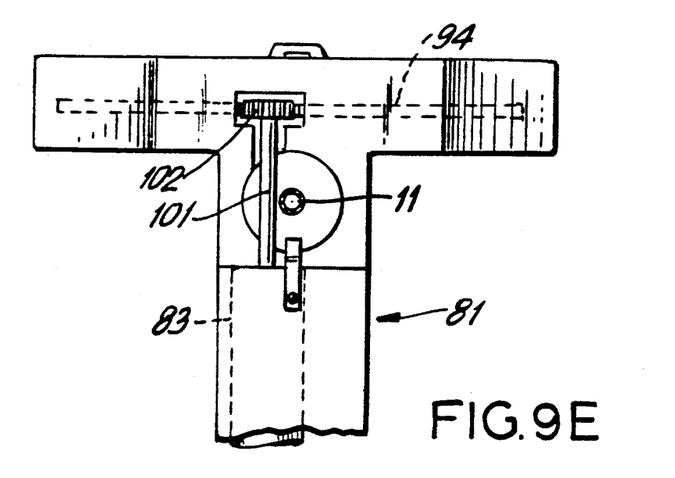
FIG. 9E is a view of the barrel portion of the liposuction device taken along line 9E—9E of FIG. 9.

Referring to FIGS. 9 through 9E, there is illustrated yet a fifth embodiment of the liposuction device of the present invention. In general, the liposuction device 1'''' has a pistol-shaped housing 2'''' which comprises a barrel portion 80 and a detachable handle portion 81. Instead of using a reciprocating piston motor to translate cannula 3 relative to housing 2'''', this embodiment utilizes a rotary-type moor 83. In operative association with a cam mechanism, generally indicated by 84, rotary-type motor 83 causes actuation element 85 to cyclically slide back and forth and cause cannula 3 to reciprocate relative to barrel portion 80 of piston-shaped hosing 2''''.

As illustrated in FIG. 9B through 9D, barrel portion 80 of the housing comprises a cannula cavity 86 for slidably receiving base 7 of the cannula, in a manner described hereinabove. Cannula cavity 86 is provided with an opening, over which a hingedly connected cover panel 88 is provided to facilitate insertion of the cannula into, and removal of the cannula from, cannula cavity 86. Cover panel 88 illustrated in FIG. 9D in greater detail, retains cannula base 7 in cannula cavity 86 when cover panel 88 is closed, as shown. To install cannula 3 into cannula cavity 86, semi-flexible transparent tubing 11 is connected to cannula outlet port 8. Then cover panel 88 is opened and tubing 11 fed out through rear port 89 of barrel portion 80, as illustrated in FIGS. 9B and 9E. Cannula base 7 is then slid into cavity 86 with a portion of actuation element 85 received in notch 9. Thereafter, cover panel 88 is snapped closed using, for example, a spring biased locking device 90, of the type previously described above. Removal of cannula 3 simply involves a reversal of the above procedure. Alternatively, using a spring biased actuation element and cannula 3' as illustrated in FIG. 4, barrel portion 80 can be realized without necessity of hinged cover panel 88. In such an alternative embodiment, cannula 3' can be snapped into and pulled out of cannula cavity 86 in a manner described hereinabove.

As illustrated in FIGS. 9B through 9E, barrel portion 80 houses cam mechanism 84 which is operably associated with (i) rotary motor 83 contained within the handle portion, and (ii) actuation element 85 slidably received within a longitudinal slot 91 formed within the upper wall of cannula cavity 86. As in the other previously described embodiments, actuation element 85 includes a projection 92 that passes through elongated slot 91 and is received within notch 9 formed in cannula base 7. With such an arrangement, as rotary motor 83 is caused to rotate under either gas pressure or electrical power, actuation element 85 is caused to reciprocate within elongated slot 91 by way of cam mechanism 84, and thereby cause cannula 3 to reciprocate relative to housing 2''''.

As illustrated in FIGS. 9A and 9B, cam mechanism 84 of the preferred embodiment comprises a drive wheel 94 having gear teeth 94A. Drive wheel 94 is rotatably mounted to a shaft 95 disposed within an accommodating portion 96 of barrel portion 80. Cam mechanism 80 also includes a connective element 97 having first and second ends 97A and 97B, respectively. First end 97A of the connective element is pivotally attached to the drive wheel 94 at a point disposed away from the axial center 95, whereas second end 97B is pivotally connected to actuation element 85 is shown. In order to adjust the distance away from the axis of rotation 95 at which the first end of the connective element is pivotally attached, a radially formed slot 98 is formed in drive wheel 94. A plurality of widened circular apertures 99 are disposed along radial slot 98 as shown in FIG. 9A, so that a spring-loaded cylindrical pin 100 passing through the first end of connective element 97, can be selectively locked into one of apertures 99 by pulling upwardly upon pin 100 and setting its cylindrical base 100B into the desired aperture 99.

In FIG. 9C, pin 100 is shown to include pin head 100C, a hollow bore 100D, axle 100E having heads 100F and 100G, with a spring 100H enclosed within bore 100D, about axle 100E and between head 100F and inner flange 100I. By selectively locking the first end of connective element 97 into a particular circular notch 99 using spring loaded pin 100, the distance of the first end of the connective element from axial center 95 can be set, and thus the amount of cannula excursion within cannula cavity 86 thereby selected. To permit access to spring-loaded pin 100, accommodating portion 96 of the housing is provided with a hinged door 110 that can be opened and snapped closed as desired.

As illustrated in FIGS. 9A and 9B, handle portion 81 of the housing encloses a substantial portion of rotary motor 83 whose shaft 101 projects beyond the handle portion and bears a gear wheel 102. As shown, gear wheel 102 has gear teeth 102A which mesh with drive wheel teeth 94A. Notably, to permit the rear portion 103 of cannula cavity 86 to extend all the way towards the rear of the barrel portion for passage and exit of aspiration hose 11, shaft 101 of the motor is mounted off center of handle portion 81, as shown in FIG. 9E. Rotary motor 83 is preferably an electric motor whose shaft speed is controllable by the voltage applied to its terminals. Such speed control can be realized by a conventional speed control circuit 105 connected in series between motor 83 and a conventional 120 volt, 50-60 Hertz power supply. Conventional electrical cord 106 can be used to connect the control circuit 105 and the power supply. Control over the voltage from the speed control unit circuit 105 to the electrical motor 83, can be adjusted by changing the resistance of a potentiometer 107 operatable connected to the speed control circuit 105. As shown in FIG. 9B in particular, this potentiometer 107 can be embodied within a trigger mechanism 108 connected, for example, to handle portion 81 of housing 2''''. By pulling trigger 108, the speed of rotary motor 83 can be controlled, and consequently, so too the rate of reciprocation of cannula 3.

To connect handle portion 81 to barrel portion 80 and permit disconnection therebetween for cleaning, sterilization and general service, handle portion 81 is provided with projection 112 and thumb-operable spring element 113, whereas barrel portion 80 is provided with slot 114, projection 115, and cavity 116. To connect handle portion 81 to barrel portion 80, shaft 101 is vertically passed through channel 117 until gear 102 is slightly below the plane of drive wheel 94. Then, spring element 113 is inserted within cavity 116 while projection 112 is guided into slot 114. By pushing the gear portion of handle 81 in the direction of cannula cavity 86, spring element 113 will snap over and clasp projection 115 as shown in FIG. 9B. In this configuration, handle portion 81 is secured to barrel portion 80 and gear teeth 102A will mesh with drive wheel teeth 94A. To disconnect handle portion 81 from barrel portion 80, the surgeon's thumb simple depresses spring-element 113 downwardly and then, by moving handle portion 81 slightly rearwardly, then downwardly, projection 112 is dislodged from slot 114 and motor shaft 101 withdrawn from channel 117. In this disassembled state, barrel portion 80 can be cleaned and sterilized using conventional procedures known in the surgical instrument art.

Liposuction device 1'''' described above employed an electric rotary motor to effectuate reciprocation of cannula 3 relative to housing 2''''. However, in an alternative embodiment, it is possible to employ a conventional gas driven rotary motor in lieu of electric rotary motor 83. In such an embodiment, trigger 108 can be operatively associated with a gas flow control valve. In such an arrangement, by controlling the rate of gas flow to the gas rotary motor upon actuation of trigger 108, the angular velocity of shaft 101 can be controlled and thus the rate of reciprocation of cannula 3 relative to housing 2''''.

Having described various illustrated embodiments, it is appropriate at this juncture to described the method of the present invention using, for purposes of illustration only, the liposuction instrument 1" illustrated in FIG. 5.

In general, the surgeon prepares in a conventional manner, the area of skin below which liposuction is to be performed. Typically, this entails marking various zones where radial excursions of the cannula is to occur. Liposuction instrument 1" of the present invention is assembled as described above so that aspiration aperture 6 of cannula 3 is in communication with a vacuum source. A small incision is then made in the patient's skin in a conventional manner, and cannula 3 is inserted into a premarked radial zone. As pressurized gas is provided to piston motor 4, cannula 3 will automatically reciprocate causing aperture 6 to automatically move within the fatty tissue. During the operation of the instrument, the surgeon's hand is maintained relatively stationary with respect to the patient and fat is aspirated through aperture 6 into a reservoir tank operably associated with the vacuum source.

As deemed necessary, the surgeon can selectively increase the rate of cannula excursion relative to the hand-holdable housing 2", by controlling the rate of gas flow to piston motor 4. This can be achieved by a foot-operated gas flow control device 44. Also, the amount of cannula excursion can also be changed by adjusting the compliance of spring 26 through rotation of threaded element 28.

While the particular embodiments shown and described above have proven to be useful in many applications in the liposuction art, further modifications of the present invention herein disclosed will occur to persons skilled in the art to which the present invention pertains, and all such modifications are deemed to be within the scope and spirit of the present invention defined by the appended claims.

What is claimed is:

1. Apparatus for use in liposuction treatment, which comprises:
   a hand-holdable housing having a first cavity;
   a cannula having a distal end and a proximal end, and at least one suction aperture about said distal end and a base operably associated with said proximal end, said cannula being insertable within said first cavity so that said cannula is free to reciprocate relative to said housing; and
   reciprocation means disposed within said housing and operable associated with said cannula so that said cannula can be selectively caused to reciprocate relative to said hand-holdable housing within said first cavity.

2. The apparatus of claim 1, wherein said cannula further comprises an outlet port and a continuous passageway extending from said suction aperture to said outlet port.

3. The apparatus of claim 1, wherein said housing further comprises retention means for releasably retaining said cannula within said first cavity.

4. The apparatus of claim 3, wherein said retention means comprises a cover panel hingedly connected to said housing and enclosing said first cavity and retaining said cannula base therein when said cover panel is disposed in a closed position.

5. The apparatus of claim 4, wherein said reciprocation means comprises a powered device operably associated with an actuation element having at least one projection which projects into said first cavity, and wherein said cannula base further includes a receiving slot into which said projection is received so as to cause said cannula to reciprocate relative to said housing when said actuation element is caused to reciprocate relative to said powered device.

6. The apparatus of claim 3, wherein said reciprocation means comprises a powered device operably associated with an actuation element in communication with said first cavity, wherein said cannula includes an indentation means in said cannula base, and wherein said retention means comprises a biased element projecting from said actuation element and being releasably received within said indentation means so as to cause said cannula to reciprocate relative to said housing when said actuation element is caused to reciprocate relative to said powered device.

7. The apparatus of claim 1, which further comprises rate control means for selectively controlling the rate at which said cannula is caused to reciprocate relative to said hand-holdable housing.

8. The apparatus of claim 1, which further comprises excursion control means for selectively controlling the amount of excursion of said cannula relative to said hand-holdable housing.

9. The apparatus of claim 6, wherein said powered device comprises a gas driven piston.

10. The apparatus of claim 9, wherein said gas driven piston further comprises a chamber housing and a movable piston slidably received within said chamber housing, said chamber housing having a gas inlet port and said movable piston having a gas outlet port, said movable piston being biased in a direction against the direction of movement of said movable piston when said chamber housing is filled with gas through said gas inlet port, and said gas outlet port permitting release of gas from said chamber housing when said movable piston undergoes a predetermined excursion against the direction of said bias, whereby said movable piston is caused to reciprocate relative to said chamber housing.

11. The apparatus of claim 10, wherein said movable piston is biased by a biasing means, and said gas is provided to said gas inlet port at a substantially constant pressure, and said actuation element is operably associated with said movable piston.

12. The apparatus of claim 11, wherein said biasing means is characterized by a variable compliance, and the rate at which said cannula is caused to reciprocate relative to said housing is selectively controlled by adjusting said compliance of said biasing means.

13. The apparatus of claim 11, wherein the rate at which said cannula is caused to reciprocate relative to said housing is selectively controlled by adjusting the rate of flow of said gas through said gas inlet port.

14. The apparatus of claim 6, wherein said powered device comprises a gas driven motor having a chamber housing and a movable piston slidably received within said chamber housing, said chamber housing having a gas inlet port and said movable piston having at least one gas outlet port, said movable piston being biased in a direction against the direction of movement of said movable piston when said chamber housing is filled with gas through said gas inlet port, and said gas outlet port permitting release of gas from said chamber housing when said movable piston undergoes a predetermined excursion against the direction of said bias, whereby said movable piston is caused to reciprocate relative to said chamber housing.

15. The apparatus of claim 14, wherein said movable piston is biased by a biasing means, said gas is provided to said gas inlet port at a substantially constant pressure, and said actuation element is operably associated with said movable piston.

16. The apparatus of claim 15, wherein said gas driven motor further comprises an intermediate housing wall slidably received within said chamber housing and said movable piston being slidably received within said intermediate housing wall, said intermediate housing wall being selectively slidable into one of a plurality of positions relative to said chamber housing so as to permit release of gas from said chamber housing through said gas outlet port in said movable piston when said movable piston undergoes a predetermined excursion against the direction of said bias, whereby said movable piston is caused to reciprocate relative to said chamber housing.

17. The apparatus of claim 16, which further comprises excursion selection means operably associated with said intermediate housing wall, for selectively setting the position of said intermediate housing wall relative to said chamber housing, so as to control the amount of excursion of said cannula relative to said hand-holdable housing.

18. The apparatus of claim 5, wherein said powered device comprises first and second gas driven motors each operably associated with an actuation element having at least one projection which projects into said first cavity, and wherein said cannula base further comprises receiving slots into which said projections are received so as to enable said cannula to reciprocate relative to said hand-holdable housing when said actuation elements are caused to reciprocate relative to respective gas driven motors, said gas driven motors being operably associated with each other so as to cause said cannula to reciprocate relative to said hand-holdable housing when said actuation elements are caused to reciprocate relative to said respective gas driven motors.

19. The apparatus of claim 18, wherein said first and second gas driven motors each comprise a chamber housing and a movable piston slidably received within said respective chamber housing, each said chamber housing having a gas inlet port and said respective movable piston being displaced from said respective chamber housing when said respective chamber housing is filled with gas through said respective gas inlet port, and each said gas outlet port permitting release of gas from said respective chamber housing when said respective movable piston undergoes a predetermined excursion, whereby each said movable piston is caused to reciprocate relative to said respective chamber housing.

20. The apparatus of claim 19, which further comprises gas flow control means operably associated with the gas inlet ports of said first and second gas driven pistons and a source of pressurized gas, said gas flow control means being capable of alternatingly diverting said pressurized gas from said source to said first chamber housing and to said second chamber housing, so as to alternatingly drive said first movable piston to a first predetermined displacement when said first chamber housing fills with gas, and to drive said second movable piston to a second predetermined displacement when said second chamber housing fills with gas, said first and second movable pistons each moving in tandem when said first or second movable piston is being driven by said gas.

21. The apparatus of claim 20, wherein said gas flow control means comprises a shuttle valve housing having first and second shuttle chambers separated by a shuttle valve capable of being moved between at least a first and a second shuttle position, said gas being diverted from said source through said first shuttle chamber to said first chamber housing when said shuttle valve is disposed in said first shuttle position, and said gas being directed from said source through said second shuttle chamber to said second chamber housing when said shuttle valve is disposed in said second shuttle position.

22. The apparatus of claim 21, wherein said gas flow control means further comprises shuttle valve actuation means for moving said shuttle valve from said first position to said second position upon a first predetermined displacement of said first movable piston, and for moving said shuttle valve from said second position to said first position upon a second predetermined displacement of said second movable piston.

23. The apparatus of claim 22, wherein said shuttle valve actuation means comprises a shaft on which said shuttle valve is fixedly mounted said shaft extending axially through opposing end walls of said shuttle valve housing, said shaft having first and second ends which are capable of being operably associated with said first and second movable pistons, respectively, upon said first and second pistons undergoing said first and second predetermined displacements, respectively.

24. The apparatus of claim 23, wherein said shuttle valve actuation means further comprises a magnetic force means disposed on one of said shuttle valve and two portions of said shuttle valve housing, so as to magnetically bias said shuttle valve towards said first and second positions when said shuttle valve is disposed at a predetermined position between said first and second shuttle positions.

25. The apparatus of claim 5, wherein said powered device comprises a rotary motor and said actuation element is operably associated with said rotary motor by a cam means so as to cause said actuation element to reciprocate along a longitudinally disposed slot formed in said first cavity, whereby said cannula is caused to reciprocate relative to said hand-holdable housing.

26. The apparatus of claim 25, wherein said cam means comprises a drive wheel rotatably mounted to a portion of said hand-holdable housing and rotatably driven by said rotary motor, and a connective element having first and second ends, said first end being pivotally connectable to a point on said rotatable wheel away from the axis of rotation thereof and said second end being pivotally connectable to said actuation element so as to cause said actuation element to reciprocate along said longitudinally disposed slot in said first cavity when said drive wheel is caused to rotate by said rotary motor, whereby said cannula is caused to reciprocate relative to said hand-holdable housing.

27. The apparatus of claim 26, wherein said hand-holdable housing comprises a barrel portion and a handle portion.

28. The apparatus of claim 27, wherein said handle portion is detachably connectable to said barrel portion.

29. The apparatus of claim 28, wherein said drive wheel, connective element and actuation element are disposed within at least a portion of said barrel portion, and wherein said rotary motor is disposed within said handle portion and operably associatable with said drive wheel when said handle portion is connected to said barrel portion.

30. The apparatus of claim 28, wherein said barrel portion contains said first cavity, and said barrel portion includes an opening for insertion of said cannula base within said first cavity and a hingedly connected cover panel which is capable of substantially enclosing and retaining said cannula within said first cavity.

31. The apparatus of claim 6, wherein said hand-holdable housing comprises a barrel portion and a handle portion.

32. The apparatus of claim 31, wherein said first cavity is formed in said barrel portion.

33. The apparatus of claim 32, wherein said handle portion is detachably connectable to said barrel portion.

34. A cannula for releasable insertion into a cannula cavity formed in a hand-holdable housing of a powered liposuction device having reciprocation means for reciprocating said cannula relative to said hand-holdable housing, said cannula comprising:

an elongated tube having a distal end and a proximal end, and at least one suction aperture about said distal end;

a base operably associated with said proximal end of said elongated tube and facilitating sliding movement of said cannula within said cannula cavity, said base further including an outlet port and a continuous passageway extending from said suction aperture to said outlet port; and at least one notch means formed in said base for operably associating said reciprocation means with said base when said cannula is inserted into said cannula cavity.

35. The cannula of claim 34, wherein said base further comprises a longitudinally extending recessed groove, and said notch means is a indentation formed along said recessed groove.

36. The cannula of claim 35, wherein said recessed groove has widened portions at each end of said base.

37. The cannula of claim 34 wherein said elongated tube and said base are integrally formed from a plastic material.

* * * * *